(12) United States Patent
Troeger et al.

(10) Patent No.: US 10,170,871 B1
(45) Date of Patent: Jan. 1, 2019

(54) CONTACT ELEMENT COMPRISING A SENSOR

(71) Applicant: HARTING ELECTRIC GMBH & CO. KG, Espelkamp (DE)

(72) Inventors: Lutz Troeger, Osnabrueck (DE); Frank Brode, Berlin (DE)

(73) Assignee: HARTING ELECTRIC GMBH & CO. KG (DE)

( * ) Notice: Subject to any disclaimer, the term of this patent is extended or adjusted under 35 U.S.C. 154(b) by 0 days.

(21) Appl. No.: 15/743,997

(22) PCT Filed: Sep. 12, 2016

(86) PCT No.: PCT/DE2016/100425
§ 371 (c)(1),
(2) Date: Jan. 11, 2018

(87) PCT Pub. No.: WO2017/045669
PCT Pub. Date: Mar. 23, 2017

(30) Foreign Application Priority Data

Sep. 17, 2015 (DE) .......................... 10 2015 115 657

(51) Int. Cl.
| | | |
|---|---|---|
| H01R 13/66 | (2006.01) |
| H01R 13/04 | (2006.01) |
| G02B 6/02 | (2006.01) |
| G01K 11/32 | (2006.01) |
| G01N 21/17 | (2006.01) |
| G02B 6/36 | (2006.01) |

(52) U.S. Cl.
CPC ..... *H01R 13/6683* (2013.01); *G01K 11/3206* (2013.01); *G01N 21/17* (2013.01); *G02B 6/02076* (2013.01); *G02B 6/3636* (2013.01); *H01R 13/04* (2013.01); *G01N 2201/088* (2013.01)

(58) Field of Classification Search
CPC .................................................. H01R 13/6683
See application file for complete search history.

(56) References Cited

U.S. PATENT DOCUMENTS 4,830,457 A * 5/1989 Asada .................... G02B 6/444
174/70 R
4,960,318 A * 10/1990 Nilsson ................ G02B 6/4407
385/103

(Continued)

FOREIGN PATENT DOCUMENTS

| CN | 102338673 | 2/2012 | ............. G01K 11/32 |
| CN | 202797505 | 3/2013 | ............. H01R 13/66 |

(Continued)

OTHER PUBLICATIONS

German Office Action (w/machine translation) issued in application No. 10 2015 115 657.1, dated May 30, 2016 (6 pgs).

(Continued)

*Primary Examiner* — James Harvey
(74) *Attorney, Agent, or Firm* — Hayes Soloway P.C.

(57) ABSTRACT

An electrical contact element with an integrated sensor is provided. The contact element has a groove, at least a portion of which extends on a plug-in side of the contact element. An optical fiber is provided in the groove. The optical fiber is designed in such a way as to be suitable as a sensor for measuring the temperature or the air humidity.

9 Claims, 1 Drawing Sheet

(56) References Cited

U.S. PATENT DOCUMENTS

| | | | | |
|---|---|---|---|---|
| 5,381,498 | A | 1/1995 | Bylander | 385/83 |
| 5,634,801 | A * | 6/1997 | Johnson | G01R 1/0433 439/71 |
| 6,102,572 | A * | 8/2000 | Hidano | F16C 29/064 384/43 |
| 6,886,977 | B2 | 5/2005 | Kaminski et al. | 374/152 |
| 2008/0013239 | A1 | 1/2008 | Kopelman | 361/103 |
| 2012/0286580 | A1 | 11/2012 | Sauerwein et al. | 307/104 |
| 2016/0333646 | A1* | 11/2016 | Olin | E21B 47/01 |
| 2017/0181646 | A1* | 6/2017 | Hayes | A61B 5/6851 |
| 2017/0196479 | A1* | 7/2017 | Liu | G01K 13/002 |
| 2018/0113155 | A1* | 4/2018 | Troger | G01R 15/181 |

FOREIGN PATENT DOCUMENTS

| | | | |
|---|---|---|---|
| CN | 202799505 | 3/2013 | H05K 7/14 |
| DE | 3832185 | 3/1990 | G01N 21/45 |
| DE | 20201632 | 6/2002 | H01R 13/66 |
| DE | 69428907 | 6/2002 | G02B 6/36 |
| DE | 102004034475 | 2/2005 | G01K 1/14 |
| DE | 202007018305 | 7/2008 | H01R 13/66 |
| DE | 102011075593 | 11/2012 | B60R 16/027 |
| EP | 0274228 | 12/1987 | G02B 6/44 |
| WO | WO0213330 | 2/2002 | H01R 13/713 |

OTHER PUBLICATIONS

International Search Report (w/translation) and Written Opinion (w/o translation) issued in application No. PCT/DE2016/100425, dated Dec. 2, 2016 (15 pgs).

International Preliminary Report on Patentability (translation) issued in application No. PCT/DE2016/100425, dated Mar. 29, 2018 (9 pgs).

* cited by examiner

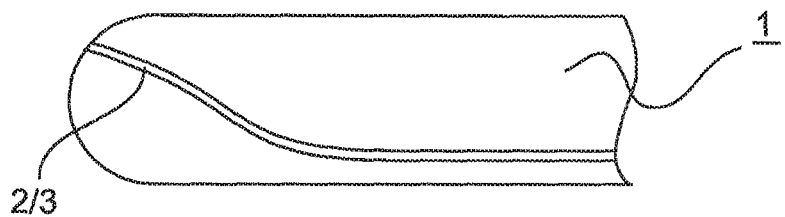
Fig.1
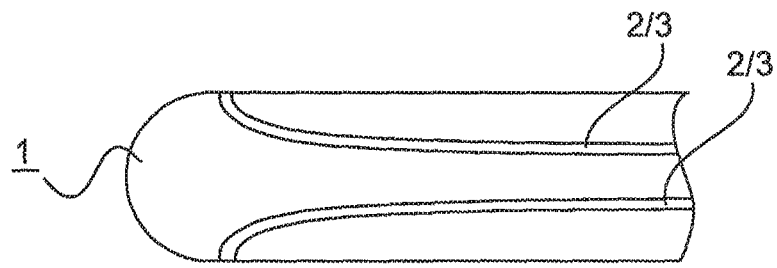
Fig.2
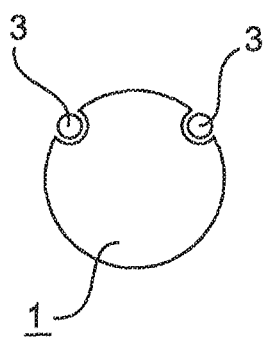 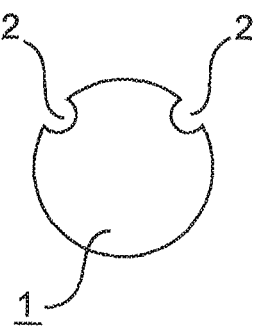 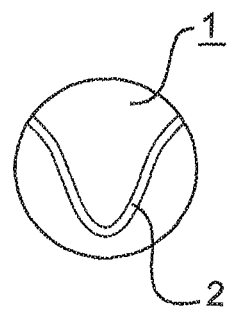
Fig.3  Fig.4  Fig.5
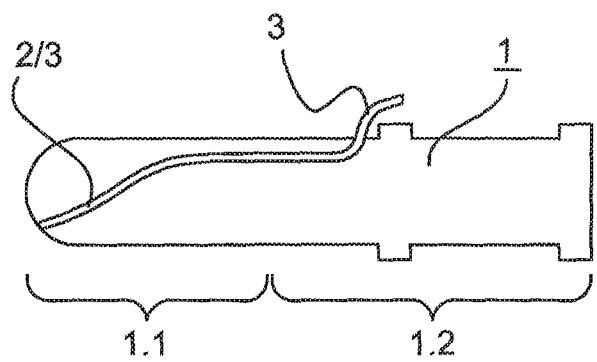
Fig.6

CONTACT ELEMENT COMPRISING A SENSOR

The invention relates to a contact element as claimed in the pre-characterizing clause of the independent claim 1.

Contact elements of this type are needed to produce an electrical contact between two lines. It is thus intended for the lines to be contacted to each other reversibly. Depending on the application and the current strength transferred, contact elements of this type can become very warm during operation. Because sometimes high transfer resistances occur at the contact points, the contact elements heat up.

PRIOR ART

In order to avoid failure of the contact elements because of excessively high temperatures, different contact elements with integrated sensors for monitoring the temperature are known from the prior art.

A measuring device on a plug-in contact is known from DE 20 2007 018 305 U1, with a plug-in region and a connection region which is arranged in a socket opening in a contact insert in a plug-in connector housing. The electrically conductive plug-in contact has, in the connection region, a recess in which a measurement sensor is embedded in an electrically non-conductive material.

A disadvantage of the contact elements known from the prior art is that, although the temperature is measured at the contact, it is not measured in the region of the contact point. The spatial separation of the measuring point and the contact point must be compensated by computer models. As a result, deviations between the actual temperature at the contact point of the contact element and the measured temperature can occur. Failure and malfunction of the contact element can thus not be excluded altogether.

OBJECT OF THE INVENTION

The object of the invention consists in providing a contact element with a sensor, wherein the measurement preferably takes place at the contact point of the contact element.

The object is achieved by the characterizing features of independent claim 1.

Advantageous embodiments of the invention are provided in the subclaims.

The invention is an electrical contact element as known from the prior art. According to the invention, the contact element has a groove in which an optical fiber runs. The groove is preferably provided on the plug-in side of the contact element. In a preferred embodiment, the groove runs directly through the contact point of the contact element.

The start and end of the groove are advantageously located on the connection side of the contact element. The optical fiber can thus pass on the connection side of the contact element into the groove and pass out of the latter. The groove thus forms a loop on the plug-in side of the contact element and in which the optical fiber is passed. In a further preferred embodiment, the groove advantageously passes in parallel from the connection side to the plug-in side.

An advantageous embodiment provides that the optical fiber is pressed into the groove and held therein. A further embodiment provides that the optical fiber is bonded into the groove.

According to the invention, the optical fiber has a so-called Bragg grating. The Bragg grating serves as an optical interference filter in the optical fiber. As a result, wavelengths lying within a filter bandwidth are reflected. The optical fiber designed in this way can consequently be used as a sensor for measuring the temperature.

The optical fiber can also be used to measure the humidity, by advantageous manipulation of the optical fiber (by the latter being split lengthwise).

As a result of the optical fiber being inserted according to the invention into the groove in the contact element, measurements can be made directly at the contact point of the contact element.

EXEMPLARY EMBODIMENT OF THE INVENTION

An exemplary embodiment of the invention is shown in the drawings and is explained in detail below. In the drawings:

FIG. 1 shows the plug-in side of a contact element;

FIG. 2 shows the plug-in side of a contact element in a further view;

FIG. 3 shows a cross-section through a contact element with an optical fiber;

FIG. 4 shows a cross-section through a contact element;

FIG. 5 shows a contact element with a view of the plug-in side; and

FIG. 6 shows a further contact element.

The drawings contain partially simplified schematic views. Identical reference numerals are used in part for the same, but possibly not identical, elements. Different views of the same elements can be at different scales.

FIG. 1 shows a plug-in side 1.1 of a contact element 1 according to the invention. A groove 2 in the contact element 1 runs along the plug-in side 1.1. The groove 2 runs as far as the tip (shown on the left) of the plug-in side 1.1. At the tip, the groove 2 runs onto the rear side and from there back to where it started.

According to the invention, an optical fiber 3 is embedded in the groove 2. The optical fiber 3 is preferably pressed or bonded into the groove 2 and runs in the latter. The course is shown again in FIG. 2. The contact element 1 is shown from a different side. The course of the groove 2, how it runs in the right-hand region parallel to the left-hand tip of the contact element 1, can be seen here. At the tip of the contact element 1, the groove 2 runs once around the tip and continues on the rear side.

A cross-section of a contact element 1 is shown in FIGS. 3 and 4. The groove 2 receives the round optical fiber 3. Depending on the design of the groove 2, the optical fiber 3 is automatically clamped in the groove 2 or is fixed in the latter, for example using adhesive.

As a result of the rounded tip of the contact element 1, a curved course of the groove 2 and the optical fiber 3 is produced at the tip. The temperature of the whole plug-in side 1.1 of the contact element 1 can be measured particularly advantageously owing to the course of the groove 2 and the optical fiber 3 over the tip of the contact element 1.

A whole contact element 1 is additionally shown in in FIG. 6. The right-hand connection side 1.2 is provided for contacting an electrical line and designed as a crimped connection. In addition, the groove 2, into which the optical fiber 3 is inserted in the connection region 1.2, begins in the connection region 1.2.

The groove 2 and the optical fiber 3 run from the connection side 1.2 to the plug-in side 1.1. The groove 2 and optical fiber 3 form a loop at the tip of the plug-in side 1.1 and run on the rear side of the contact element 1 back to the connection side 1.2.

The invention claimed is:

1. An electrical contact element comprising at least one groove with an optical fiber running in the groove wherein the optical fiber is designed as a sensor, and the groove starts at a connection side, remote from a plug-in side, of the contact element and runs to the plug-in side and ends again at the connection side.

2. The electrical contact element as claimed in claim 1, wherein the start and end of the groove run in parallel from the connection side to the plug-in side and are connected to each other on the plug-in side.

3. The electrical contact element as claimed in claim 1, wherein the groove forms a loop on the plug-in side.

4. The electrical contact element as claimed in claim 2, wherein the groove forms a loop on the plug-in side.

5. The electrical contact element as claimed in claim 1, wherein the optical fiber is pressed into the groove.

6. The electrical contact element as claimed in claim 1, wherein the optical fiber is bonded into the groove.

7. The electrical contact element as claimed claim 1, wherein the optical fiber has a Bragg grating.

8. The electrical contact element as claimed in claim 1, wherein the optical fiber is designed as a temperature sensor.

9. The electrical contact element as claimed in claim 1, wherein the optical fiber is designed as a humidity sensor.

\* \* \* \* \*